United States Patent [19]

Jones et al.

[11] 3,963,648

[45] June 15, 1976

[54] PERFUME CHEMICALS

[75] Inventors: Barry Nicholas Jones, Ingrove;
Hifzur Rahman Ansari, London;
Brian George Jaggers, Romford;
John Francis Janes, Epping, all of
England

[73] Assignee: Bush Boake Allen Limited,
Walthamstow, England

[22] Filed: May 15, 1974

[21] Appl. No.: 470,282

Related U.S. Application Data

[63] Continuation-in-part of Ser. No. 311,710, Dec. 7, 1972, abandoned.

[30] Foreign Application Priority Data

Sept. 8, 1972 United Kingdom............... 41845/72

[52] U.S. Cl............................. 252/522; 260/675.5
[51] Int. Cl.² ..................... A61K 7/46; C11B 9/00
[58] Field of Search................... 252/522; 260/675.5

[56] References Cited
UNITED STATES PATENTS 2,871,268  1/1959  Bain et al........................ 260/675.5

FOREIGN PATENTS OR APPLICATIONS 859,567  1/1961  United Kingdom................. 252/522
859,568  1/1961  United Kingdom................. 252/522

OTHER PUBLICATIONS

Chem. Ab., 67, 22024w, 1967.

Chem. Ab., 72, 121721f, 1970.

Kulka, J. Agr. Food Chem., 19, No. 6, 1074–1075, 1971.

*Primary Examiner*—C. Davis
*Attorney, Agent, or Firm*—Flynn & Frishauf

[57] ABSTRACT

A compounded perfumery composition comprising component A and component B, component B being from 0.1 to 95% by weight based on the weight of said compounded perfumery composition. Component B comprises at least one compound of the formula wherein R is at least one group selected from methyl, ethyl, propyl, iso-propyl, n-butyl, sec-butyl, tert-butyl, pentyl or hexyl.

19 Claims, No Drawings

PERFUME CHEMICALS

This application is a continuation in part of our application serial number 311710 filed Dec. 7th 1972 now abandoned.

This invention relates to perfumery compositions of the type where a number of odoriferous materials, of synthetic or natural origin, are admixed or compounded to form a perfumery concentrate. Such concentrates may find use as such or after dilution but more usually they are added in small proportions to other materials such as to space sprays or to soap, detergent, cosmetic or deodorant compositions or to substrates such as fabrics, fibres or paper products, in order to provide them with agreeable olfactory properties. Thus, such concentrates are products of commerce and perfumery concentrates may comprise a simple or complex mixture of individual perfumery compounds.

From one aspect the invention provides compounded perfumery compositions comprising a plurality of odoriferous perfumery ingredients and one or more compounds having the formula

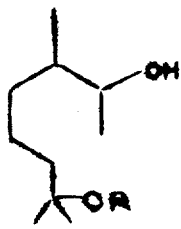

where R is an alkyl group having from 1 to 6 carbon atoms. Such compounds may be individual stereoisomers or mixtures of the individual diasteroisomers having the aforesaid formula.

It has been discovered that these compounds (which will hereinafter be referred to as alkoxyelgenol derivatives) have a marked sandalwood odour with citrous undertones, reminiscent also of rose, with a powerful and long lasting sandalwood/rose middle note. This sandalwood character is most surprising since the saturated $C_{10}$ acrylic terpenoids generally do not have odours of this type which have hitherto been most commonly associated with the presence of an isobornyl group. Moreover, the closest known homologues to the compounds of the invention e.g., as described in West German Auslegeschrift 1232563 such as elgenol (2, 6 dimethyl octan 2-7 diol) and methoxycitronellol (2, 6 dimethyl 1-2 methoxy octan 8 - ol) exhibit no trace of any sandalwood odour. West German Auslegeschrift 1232563 describes a process for producing citronellol derivatives by reducing 2-6 dimethyl octan 7, 8 epoxides which are substituted in the 2 position by a hydroxy, alkoxy or acyloxy group, which process inevitably produces mixtures of citronellol and elgenol derivatives. In particular the reduction of 2, 6 dimethyl 2 methoxy octan 7, 8 epoxide is described which produces a mixture of methoxy citronellol and methoxy elgenol which is an unwanted byproduct whose isolation is not described. It follows that the odour of methoxy elgenol is not described and nowhere is the surprising sandalwood note possessed by the alkoxyelgenols described.

It has been found, moreover, that the alkoxy elgenols are suited for blending with an extremely wide range of perfumery compositions, particularly those having a floral or citrus woody odour type.

The novel perfumery compositions may be compounded according to recognised techniques of perfumery employing known odiferous perfumery ingredients, e.g., techniques and ingredients mentioned in the standard textbooks "Soap, Perfumery and Cosmetics" by W. A. Poucher, 7th edition; published by Chapman & Hall (London), 1959; "Perfume and Flavour Chemicals" by S. Arctander, published by the author (Montclair) 1959 and "Perfume and Flavour Materials of Natural Origin" also by S. Arctander, self-published, Elizabeth NJ, 1960. Specific odoriferous ingredients which may be blended with the methoxy elgenol include vetivert oil, vetiverol, vetiveryl acetate, guaiac wood oil, guaiac wood acetate, coumarin, musk ketone, lauric aldehyde, benzyl acetate, lemon oil, dimethyl benzyl carbinol, dimethyl benzyl carbinyl acetate, rose absolute, jasmin absolute, ionones, iso nonyl acetate, methyl phenyl acetate, myrcenyl iso butyrate β-phenyl ethanol, citronellol, citronellal, hydroxycitronellal, geranium oil, geraniol, linalol, nerol, lanvandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdamun resin, methyl ionones, guaioxide, orange oil, vanillin, ethylvanillin, olibanum resin, musk ambrette, rhodinol, mandarin oil, methyl nonyl acetaldehyde, neroli oil, cedrol, oakmoss, w-hydroxy longifolene eugenol, isoeugenol, cedarwood oil.

Particularly preferred odoriferous ingredients for blending with the alkoxy elgenols include:

Phenyl Ethyl Alcohol
Para Tertiary Butyl Cyclo Hexyl Acetate
Oakmoss
Musk Ketone
Coumarin
Patchouli Oil
Hydroxycitronellal
Methyl Nonyl Acetaldehyde
Labdanum
Linalol
Benzyl Benzoate
Vetiveryl Acetate
Citronellol
Methyl Ionone
Ethylene Brassylate
Geraniol
Sandalwood substitutes of the terpino-phenol type It has been found that these compounds blend especially surprisingly and harmoniously with the alkoxy elgenols of the invention and compounded perfumery compositions comprising a plurality of odoriferous ingredients including one of those preferred materials as aforesaid and one or more of the said alkoxy elgenols from a preferred aspect of the invention.

The group R in the alkoxy elgenols may be methyl, ethyl, n -, sec - or tert-butyl, a pentyl, hexyl or benzyl group. The preferred compounds of the invention are those wherein R is a methyl, ethyl or a propyl group.

Certain of the alkoxy elgenols are believed to be novel. Thus, compounds having the formula

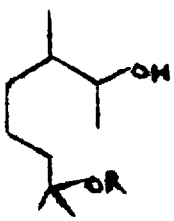

where R is an ethyl, propyl or iso-propyl, n -, sec -, or tert-butyl, pentyl or hexyl group constitute a further aspect of the invention.

Because of the exceptional utility of the alkoxy elgenols it is possible to employ them in perfumery compositions in a wide range of proportions, say 0.1 to 95% by weight on the compounded perfumery composition. A minimum proportion of 0.2 to 5% say 1–2% will be used in most cases.

The compounded perfumery compositions of the invention find use in a wide variety of perfumed materials. For example they may be used in space sprays or can be blended in soap, detergent or deodorant compositions including bath salts, shampoos, toilet waters or in cosmetic preparations such as cologne waters, toilet waters, face creams, talcum powder, body lotions, sun cream preparations and male toilet products such as shave lotions and creams. The compositions can also be used to perfume substrates such as fibres, fabrics and paper products.

The alkoxy elgenols may be prepared by standard techniques. A convenient starting material is dihydromyrcene (2, 6-dimethylocta-2, 7-diene) itself available from hydrogenation of myrcene, a pyrolysis product of β-pinene. Dihydromyrcene may be converted to a 2-alkoxy-2, 6-dimethyl-oct-7-ene by reaction with an alcohol ROH in the presence of an acid catalyst e.g. concentrated sulphuric acid, HCl, p-toluene sulphonic acid or a cation exchange resin containing sulphonate groups. Reaction temperatures may be from room temperature to the reflux temperature of the alcohol, an excess of the alcohol, e.g. a molar ratio of 2:1 to 4:1 alcohol:dihydromyrene, is desirable. Alternatively, the 2-alkoxy-2, 6-dimethyloct-7-ene may be obtained by hydrochlorination of dihydromyrcene to give 2-chloro-2, 6-dimethyloct-7-ene and reaction of the latter with sodium alkoxide NaOR. The product of this reaction may be converted to an alkoxy elgenol by epoxidation of the 7-8 double bond followed by hydrogenation.

The epoxidation may be carried out by a process such as described in UK patent No. 859,568 e.g. by formation of a chlorohydrin followed by treatment with a base or by direct reaction with a known organic peroxide epoxidising agent. The hydrogenation step is preferably carried out using Raney nickel catalyst and in the presence of a mild base such as sodium carbonate or preferably triethylamine. This addition of base is in contrast to the prior art and favours the formation of a larger proportion of elgenol derivative (~60%) over the prior art which produced elgenol derivatives as a by-product in yield of ~20%. Conveniently 0.5 to 10%, preferably from 1–2% by weight of both catalyst and base expressed on the weight of epoxides, may be used.

The invention is illustrated by the following examples:

EXAMPLE 1

A solution of 186 g, 7, 8-epoxy-2-methoxy-2, 6-dimethyloctane and 5 g sodium carbonate in 100 ccs isopropanol was hydrogenated in the presence of 2 g Raney nickel at 120°C and 150 psi hydrogen pressure over 16 hours. The product was filtered and fractionally distilled to give 75 g methoxy-citronellol and 105 g methoxyelgenol. (R=Methyl). Methoxyelgenol has a marked long lasting sandalwood odour with rose undertones.

Methoxyelgenol is a colourless liquid boiling at 84°C (1mm); $nD^{20}$ 1.4460; $d^{20}$ 0.9001; strong IR absorption peaks at 3500, 1090, 930 cms$^{-1}$:

EXAMPLE 2

An exactly analogous process was carried out using 186 gm of 7, 8 epoxy-2- ethoxy 2, 6 dimethyloctane. 75 gm of ethoxyelgenol was obtained by fractional distillation.

The odour of ethoxyelgenol was slightly more intense than the methoxy compound and had a more marked sandalwood note.

EXAMPLE 3

An exactly analogous process was carried out using 186 gm of n-propoxy epoxide. 90 gm of n-propoxy elgenol was obtained by fractional distillation.

The odour of this compound was less intense than the methoxy compound and had a slightly more pronounced floral character which was reminiscent of lilly of the valley.

EXAMPLE 4

A sandalwood type perfumery composition suitable for blending into soaps was prepared according to the following formulation:

| | |
|---|---|
| Alkoxyelgenols | 15 |
| Ethylene Brassylate | 3 |
| Cyclocitronellene Acetate | 10 |
| Methyl Ionone | 3 |
| Patchouli Oil | 1 |
| Geranium Synthetic | 5 |
| Musk Ketone | 1 |
| Phenyl Ethyl Alcohol | 15 |
| Amyl Cinnamic Aldehyde | 5 |
| Hydroxycitronellal | 10 |
| Methyl Nonyl Acetaldehyde* | 4 |
| Iso Eugenol | 1 |
| Propylene Glycol | 7 |
| Synthetic Sandalwood | 2 |
| Vetiveryl Acetate | 1 |
| Labdanum Oil | 0.5 |
| Citronellyl Acetate | 5 |
| Geraniol 98% | 3 |
| Para Tert Butyl Cyclohexyl Acetate | 5 |
| Valanone | 3.5 |
| | 100.0 |

*(10% w/w solution in diethyl phthalate)

This composition had a pleasant woody/floral odour pattern suitable for incorporation into high quality soaps.

EXAMPLE 5

A compounded perfumery composition with rose type odour was prepared according to the following formulation:

| | |
|---|---|
| Methoxyelgenol | 5.0 |
| Aldehyde C$_9$ (10% in DEP*) | 0.5 |
| Aldehyde C$_{10}$(10% in DEP*) | 0.5 |

-continued

| | |
|---|---|
| Geranium Synthetic | 5.0 |
| Geraniol Pure | 20.0 |
| Geranyl Acetate | 5.0 |
| Hydroxcitronellal | 6.0 |
| Linalol Pure | 10.0 |
| Methyl Ionone | 3.0 |
| Musk Ketone | 2.0 |
| Phenyl Ethyl Alcohol | 43.0 |
| | 100.0 |

*Diethyl Phthalate

EXAMPLE 6

A fougere type perfumery composition was prepared according to the following formulation:

| | |
|---|---|
| Methoxyelgenol | 15.0 |
| Coumarin | 5.0 |
| Musk Ketone | 4.0 |
| Benzyl Acetate | 8.0 |
| Benzyl Salicylate | 10.0 |
| Labdanum Resin 50% DEP | 2.0 |
| Geranium Synthetic | 10.0 |
| Amyl Cinnamic Aldehyde | 4.0 |
| Geraniol | 6.0 |
| Lavandin | 10.0 |
| Linalol Pure | 5.0 |
| Terpinyl Acetate | 6.0 |
| Oakmoss True Green | 5.0 |
| Patchouli Oil | 5.0 |
| | 95.0 |

EXAMPLE 7

A compounded perfumery composition with a citrous type odour was prepared according to the following formulation:

| | |
|---|---|
| Methoxyelgenol | 1.0 |
| Aldehyde C$_{12}$(Lauric 10% in DEP) | 1.0 |
| Aldehyde C$_{12}$(MNA 10% in DEP) | 1.0 |
| Bergamot Synthetic | 6.5 |
| Clary Sage | 3.5 |
| Gabanum Oil | 1.0 |
| Hydroxycitronellal | 10.0 |
| Para Tert Butyl Cyclo Hexyl Acetate | 10.0 |
| Lavander Oil French | 5.0 |
| Lemon Oil Silician | 5.0 |
| Orange Oil | 8.0 |
| Patchenol | 4.0 |
| Petitgrain Paraguay | 3.0 |
| Pine Needle Oil European | 5.0 |
| Limonene | 20.0 |
| | 84.0 |

EXAMPLE 8

The following alkoxyelgenols were prepared by the methods of examples 1-3 using the same molecular proportions and were found to have the following odours:

n—Butoxyelgenol — A marked sandalwood odour similar to that of ethoxyelgenol.

iso—Butoxyelgenol — A more pronounced floral character with a mild sandalwood character.

n-Pentoxyelgenol — A marked woody odour with a less pronounced sandalwood character.

iso-Propoxyelgenol — Reduced sandalwood odour with a more pronounced floral character.

The embodiments of the invention in which an exclusive property or priviledge is claimed are defined as follows:

1. A compounded perfumery composition comprising component A and component B, component A comprises a plurality of perfumery ingredients other than the perfumery ingredients defined as component B component B comprises at least one compound of the formula

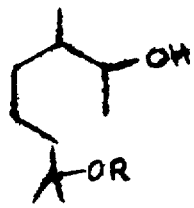

where R is at least one group selected from methyl, ethyl, propyl, iso-propyl, n-butyl, sec-butyl, tert-butyl, pentyl or hexyl, component B being from 0.1 to 95% by weight based on the weight of said compounded perfumery composition.

2. A composition according to claim 1 which has a floral type odour.

3. A composition according to claim 2 wherein component A contains at least one perfumery ingredient selected from the group consisting of phenyl ethyl alcohol, p-tert-butyl-cyclohexyl acetate; oakmoss; musk ketone, coumarin; patchouli oil; hydroxycitronellal; methyl nonyl acetaldehyde labdanum; linamol, benzyl benzoate; vetiveryl acetate; citronellol; methyl ionone; ethylene brassylate; geraniol and terpinophenol sandalwood substitutes.

4. A composition according to claim 1 wherein said component B is at least 1% by weight of said perfumery composition.

5. A composition according to claim 3 wherein said component B is at least 1% by weight of said perfumery composition.

6. A composition according to claim 5 wherein R is methyl.

7. A composition according to claim 5 wherein R is an alkyl group having firm 1 to 6 carbon atoms.

8. A composition according to claim 5 wherein R is selected from the group consisting of ethyl, n-propyl and iso-propyl.

9. A composition according to claim 1 wherein R is methyl.

10. A composition according to claim 1 wherein R is an alkyl group having from 1 to 6 carbon atoms.

11. A composition according to claim 1 wherein R is selected from the group consisting of ethyl, n-propyl and iso-propyl.

12. A composition according to claim 3 which has a citrus-woody type odour.

13. A compounded perfumery composition comprising component A and component B component A comprises at least one perfumery ingredient selected from the group consisting of vetivert oil, vetiverol, vetiveryl acetate, guaiac wood oil, guaiac wood acetate, courmain, musk ketone, lauric aldehyde, benzyl acetate, lemon oil, dimethyl benzyl carbinol, dimethyl benzyl carbinyl acetate, rose absolute, jasmin absolute, ionones, iso nonyl acetate, methyl phenyl acetate, myrcenyl iso butyrate β-phenyl ethanol, citronellol, citronellal, hydroxycitronellal, geranium oil, geraniol, linalol, nerol, lavandin oil, linalyl acetate, patchouli oil, petitgrain oil, bergamot oil, heliotropin, ethylene brassylate, undecyl aldehyde, cinnamalehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdamun resin, methyl ionones, guaioxide, orange oil, vanillin, ethylvanillin, olibanim resin, musk ambrette, rhodinol, mandarin oil, methyl nonyl acetaldehyde, neroli oil, cedrol, oakmoss, w-hydroxy longifolene eugenol, iso-eugenol, and cedarwood oil component B comprises at least one compound of the formula

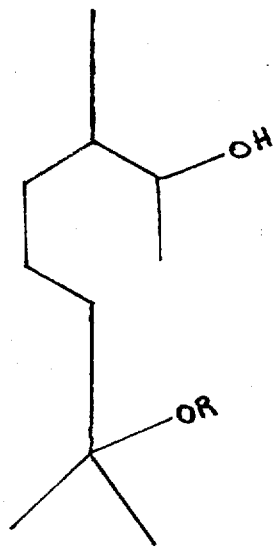

wherein R is at least one group selected from methyl, ethyl, propyl, iso-propyl, n-butyl, sec-butyl, tert-butyl, pentyl or hexyl, component B being from 0.1 to 95% by weight based on the weight of said compounded perfumery composition.

14. A composition according to claim 17 wherein component A contains at least one perfumery ingredient selected from the group consisting of phenyl ethyl alcohol, p-tert-butyl-cyclohexyl acetate; oakmoss; musk ketone, coumarin; patchouli oil, hydroxycitronellal; methyl nonyl acetaldehyde labdanum; linamol, benzyl benzoate; vetiveryl acetate; citronellol; methyl ionone; ethylene brassylate; geraniol and terpinophenol sandalwood substitutes.

15. A composition according to claim 14 wherein said component B is at least 1% by weight of said perfumery composition.

16. A composition according to claim 15 wherein R is methyl.

17. A composition according to claim 13 which has a floral-type odor.

18. A composition according to claim 13 which has a citrus-woody-type odor.

19. A composition according to claim 1 wherein said component A contains at least one perfumery ingredient selected from the group consisting of vetivert oil, vetiverol, vetiveryl acetate, guaiac wood oil, guaiac wood acetate, courmain, musk ketone, lauric aldehyde, benzyl acetate, lemon oil, dimethyl benzyl carbinol, dimethyl benzyl carbinyl acetate, rose absolute, jasmin absolute, ionones, iso nonyl acetate, methyl phenyl acetate, myrcenyl iso butyrate β-phenyl ethanol, citronellol, citronellal, hydroxycitronellal, geranium oil, geraniol, linalol, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdamun resin, methyl ionones, guaioxide, orange oil, vanillin, ethylvanillin, olibanim resin, musk ambrette, rhodinol, mandarin oil, methyl nonyl acetaldehyde, neroli oil, cedrol, oakmoss, w-hydroxy longifolene eugenol, iso-eugenol, and cedarwood oil.

* * * * *

UNITED STATES PATENT OFFICE
CERTIFICATE OF CORRECTION

Patent No. 3,963,648            Dated June 15, 1976

Inventor(s) BARRY NICHOLAS JONES et al

It is certified that error appears in the above-identified patent and that said Letters Patent are hereby corrected as shown below:

Column 2, line 16, delete "methoxy" and in its place insert --alkoxy--.

Column 2, line 47, correct the spelling of "Linalool".

Column 8, line 1, replace "17" with --13--.

Signed and Sealed this

Thirtieth Day of November 1976

[SEAL]

Attest:

RUTH C. MASON
*Attesting Officer*

C. MARSHALL DANN
*Commissioner of Patents and Trademarks*